(12) United States Patent
McFee

(10) Patent No.: US 6,400,975 B1
(45) Date of Patent: Jun. 4, 2002

(54) APPARATUS AND METHOD FOR CONSISTENT PATIENT-SPECIFIC ELECTRODE POSITIONING FOR EKG TESTING AND DELIVERY OF ELECTRICAL ENERGY TO THE HEART

(76) Inventor: Robin B. McFee, 12 A Ellis Dr., Worcester, MA (US) 01609

( * ) Notice: Subject to any disclaimer, the term of this patent is extended or adjusted under 35 U.S.C. 154(b) by 0 days.

(21) Appl. No.: 09/609,079

(22) Filed: Jun. 30, 2000

Related U.S. Application Data

(63) Continuation-in-part of application No. 08/911,390, filed on Aug. 14, 1997, now Pat. No. 6,115,623.

(51) Int. Cl.$^7$ .................................................. A61B 5/04
(52) U.S. Cl. ...................... 600/372; 600/382; 600/391; 600/392; 600/393; 607/142
(58) Field of Search ............................... 600/372–394, 600/509; 607/152, 142, 148, 149

(56) References Cited

U.S. PATENT DOCUMENTS

| | | | |
|---|---|---|---|
| 3,862,633 A | * | 1/1975 | Alison et al. ................ 128/642 |
| 4,033,333 A | * | 7/1977 | DeSalvo et al. ............. 128/642 |
| 4,121,575 A | * | 10/1978 | Mills et al. .................. 128/642 |
| 4,202,344 A | * | 5/1980 | Mills et al. .................. 128/642 |
| 4,381,012 A | * | 4/1983 | Russek ........................ 128/642 |
| 4,432,368 A | * | 2/1984 | Russek ........................ 128/642 |
| 4,498,480 A | * | 2/1985 | Mortenson .................. 128/642 |
| 4,573,474 A | * | 3/1986 | Scibetta ....................... 128/642 |
| 4,583,549 A | * | 4/1986 | Manoli ........................ 128/642 |
| 4,593,698 A | * | 6/1986 | Athans ........................ 128/642 |
| 4,751,928 A | * | 6/1988 | Hallon et al. ............... 128/642 |
| 4,832,608 A | * | 5/1989 | Kroll .......................... 128/642 |
| 4,854,323 A | * | 8/1989 | Rubin ......................... 128/642 |
| 4,955,381 A | | 9/1990 | Way et al. ................... 128/640 |
| 5,042,481 A | * | 8/1991 | Suzuki et al. ............... 128/642 |
| 5,080,099 A | | 1/1992 | Way et al. ................... 128/640 |
| 5,184,620 A | | 2/1993 | Cudahy et al. ............. 128/639 |
| 5,191,886 A | * | 3/1993 | Paeth et al. ................. 128/642 |
| 5,224,479 A | * | 7/1993 | Sekine ........................ 128/642 |
| 5,309,910 A | * | 5/1994 | Edwards et al. ............ 128/642 |
| 5,313,952 A | * | 5/1994 | Hoch .......................... 128/642 |
| 5,341,806 A | * | 8/1994 | Gadsby et al. .............. 128/642 |
| 5,370,116 A | * | 12/1994 | Rollman et al. ............ 128/642 |
| 5,445,149 A | * | 8/1995 | Rotolo et al. ............... 128/642 |
| 5,458,124 A | * | 10/1995 | Stanko et al. ............... 128/696 |
| 5,713,925 A | | 2/1998 | Sullivan et al. ............... 607/4 |
| 5,788,633 A | * | 8/1998 | Mahoney ..................... 600/382 |
| 5,938,597 A | | 8/1999 | Stratbucker ................. 600/382 |
| 5,995,861 A | * | 11/1999 | Price .......................... 600/372 |

* cited by examiner

Primary Examiner—Linda C. M. Dvorak
Assistant Examiner—David M. Ruddy
(74) Attorney, Agent, or Firm—Banner & Witcoff, Ltd.

(57) ABSTRACT

A patient-specific electrode positioning apparatus and method allow EKG testing and delivery of therapeutic electrical impulses to the heart to be performed in an accurate and consistent manner by eliminating individual positioning of precordial electrodes for all but the first EKG test on a particular patient. Each electrode is slidably mounted on a platform aligned on the torso of the patient. Each electrode is adjusted until it is properly positioned and then it is permanently fixed in place by a lock-down mechanism, leaving the electrodes permanently positioned on the platform so that, when the platform is aligned properly on the particular patient's torso utilizing an adjustable position indicator, the electrodes will be properly positioned for a repeat administration of the EKG test and for delivery of therapeutic electrical impulses.

20 Claims, 8 Drawing Sheets

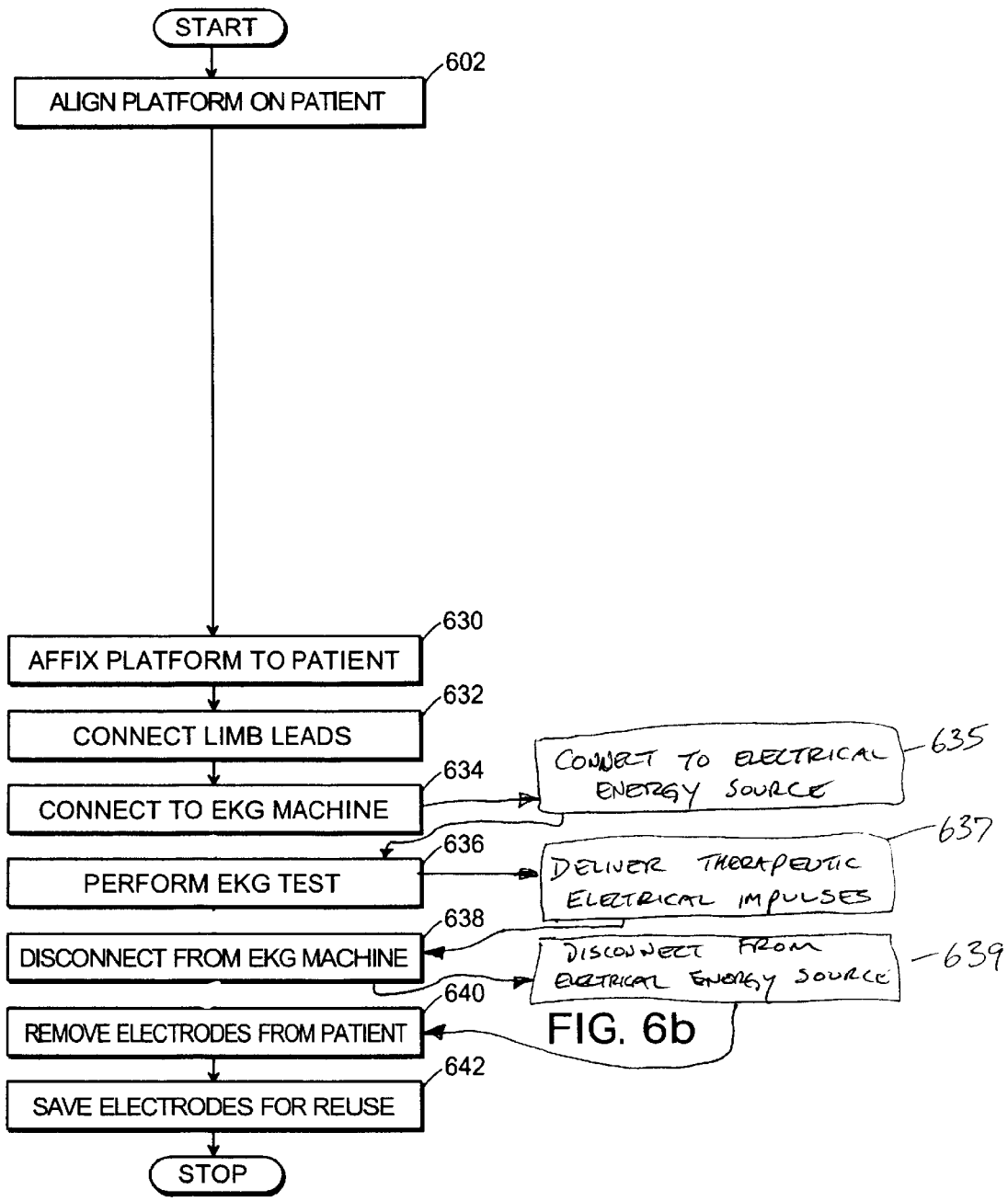

APPARATUS AND METHOD FOR CONSISTENT PATIENT-SPECIFIC ELECTRODE POSITIONING FOR EKG TESTING AND DELIVERY OF ELECTRICAL ENERGY TO THE HEART

RELATED APPLICATION

This application is a continuation-in-part of U.S. Ser. No. 08/911,390, filed on Aug. 14, 1997 now U.S. Pat. No. 6,115,623.

FIELD OF THE INVENTION

This invention relates to medical test devices, methods and systems, and more particularly to devices, methods and systems for consistently and accurately measuring and mapping cardiac function, and simultaneously delivering electrical energy to the heart.

BACKGROUND

The heart is composed of a specialized system of cells that generate and conduct electrical impulses; it is these cells which are responsible for propagating muscle contraction, thus facilitating the pumping function of the heart. While over 90 percent of the heart's mass is comprised of muscle fibers, the remaining specialized conduction tissues are distributed throughout the heart in order to enable contraction to be well synchronized. The heart is comprised of 4 chambers: 2 atria and 2 ventricles. Normally cardiac impulses are generated in the sino-atrial (SA) node, located in the right atrium. The signals then pass to the left atrium, and down the bundle of His towards the left and right ventricular bundles. Once arriving at these bundles, the impulse is distributed throughout the ventricles, enabling them to contract, thus pumping blood throughout the pulmonary and systemic circulations. The ventricles are capable of initiating an impulse if the normal SA pathway is disrupted, albeit at a much slower rate. Deviations from the normal pattern often lead to a variety of symptoms, and can predispose the patient to several serious clinical problems including sudden cardiac death (SCD). Problems with the cardiac conduction system are frequently called arrhythmias or dysrhythmias. Dysrhythmias in which the heart beats too slowly often require a pacemaker to raise the rate to more physiologic levels. Ventricular dysrhythmias whereby the heart beats too rapidly, often called tachycardia, can devolve into a life threatening emergency called ventricular fibrillation, which requires defibrillation to treat.

A variety of cardiac disease processes can contribute to the heart beating too slowly to provide appropriate cardiac output. When this occurs, often a pacemaker is required to reestablish proper heart rate. Cardiac pacing, or electrostimulation, involves sending signals from an electrical generator to the heart in order to initiate or sustain a heart rate that is physiologically appropriate. There are a variety of methods to apply such technology, including transthoracic, thransvenous and permanent pacemakers. Transcutaneous pacemakers involve placing electrodes on the skin of the patient, usually one on the chest, and one on the back, in order to deliver high energy impulses. This method is usually reserved for emergency pacing.

In the majority of patients dying suddenly from sudden cardiac death (SCD), primary electrical failure occurs, usually in the form of ventricular fibrillation. Fibrillation is chaotic, asynchronous electrical activity of the heart. The impulse in this dysrhythmia spreads erratically along a variety of changing pathways, instead of originating from a single site, usually the SA node, and then spreading in a highly ordered manner. These fibrillatory impulses result in the different regions of the heart muscle being depolarized randomly in relation to the other areas of the myocardium. Because there is simultaneous relaxation and contraction of the heart muscle cells, depending upon their relation to the fibrillation impulses, there is complete disruption of ventricular contraction, and the loss of pump function. Circulatory collapse ensues, unless rapid and appropriate advanced cardiac life support (ACLS) is initiated.

ACLS involves supplementing basic cardiopulmonary resuscitation with additional interventions, including electrocardiographic monitoring and external pacemaker devices or defibrillation. Successful treatment of patients in ventricular fibrillation depends upon reaching the patient early in the event, and initiating definitive therapy rapidly. Once on the scene, one of the rate limiting steps is the 2 step process of applying electrodes to monitor for the dysrhythmias to define the cardiac mechanism, then applying the defibrillation paddles to deliver the charge to the patient's heart.

Electrical defibrillation is a method used to terminate ventricular fibrillation. It can also be used to terminate atrial and ventricular tachydysrhythmias. The procedure involves placing two paddle electrodes on the chest, and delivering a high-energy shock wave to the heart. If the shock energy is sufficiently powerful, it will depolarize the heart cells, allowing the sinus node to resume initiating cardiac impulses in a more coordinated manner. The objective is to use the lowest amount of energy possible. Unfortunately the large electrode area and skin resistance create the need for larger amounts of energy to be used, which predisposes the patient to discomfort and burns. The energy required to terminate ventricular fibrillation is between 200–400 Joules, depending upon the underlying cardiac pathology, the body habitus of the patient, and the orientation of the heart within the chest cavity. More energy is required to overcome size and resistance. The energy of the electrical discharge can cause myocardial injury.

The process of defibrillation is subject to similar procedural and anatomic problems found in obtaining electrocardiograms (ECG or EKG). The current state of the art involves placing 2 electrodes on the patient's chest. It is well known that fibrillatory signals do not propagate in a coordinated or linear manner simplistically as north to south, left to right. Also, we know resistance to the delivered shock is patient dependent.

It is widely accepted that the success of scientific testing and therapeutic interventional procedures is based upon two criteria: 1. Reproducibility, and 2. Accuracy. Nowhere are these more critically essential than in medicine, especially cardiology, where lives often hang in the balance relying on the results.

The EKG has long been an important diagnostic tool in the field of cardiology. The EKG is used to measure the timing and amplitude of the electrical signal from the subject's heart, presenting the measurements as a visual display. The standard "twelve-lead" EKG involves the separate placement on the patient's body of ten individual electrodes, six precordially and one each on each of the four limbs. The ten electrodes are attached one at a time and must each be placed over a specific point on the patient's body. If any of the precordial electrodes are mixed up with each other, or if the arm or leg electrodes are swapped over, the EKG tracing obtained will be faulty.

The six precordial electrodes are placed on the patient's chest at specific recording zones over the heart. V1 is properly positioned in the fourth intercostal space to the immediate right of the sternum. V2 is also located in the fourth intercostal space, but to the immediate left of the sternum. V4 is positioned in the fifth intercostal space at the midclavicular line. V5 and V6 are similarly located in the fifth intercostal space, but at the anterior axillary and midaxillary lines respectively. Finally, V3 is positioned midway between V2 and V4.

The process of obtaining an EKG tracing is fraught with potential errors. In particular, the technician may make mistakes either in placing the electrodes or in reading the tracing. This is particularly likely in an emergency situation, when the test often must be administered in a hurry and the patient is frequently sweaty, immobile, and minimally cooperative. Further variability and error, in the form of discordant respiratory artifact, is introduced due to the fact that the six precordial electrodes move independently with the patient's respiration, causing noise or spurious signals. Similarly, error is introduced into EKGs performed during stress testing due to the independent motion of the six precordial electrodes, leading to multiple discordant body motion artifact (BMA).

In particular, many studies support the fact that there is a lack of reproducibility in EKG tracings obtained for the same patient due to variations in electrode placement, resulting consequently in errors in test interpretation and even in potential misdiagnosis. [See, e.g., Herman, Michael V. et al.,"Variability of Electrocardiograph Precordial Lead Placement: A Method to Improve Accuracy and Reliability," *Clin. Cardiol.,* Vol. 14, pp. 469–476 (1991).] Since today's EKG machines now handle most of the measurement and recording functions electronically, placement of the electrodes is normally the principal variable subject to error in the administration of the test. Many times patients are even subjected to unnecessary hospital stays because it is impossible for the physician to determine whether observed EKG variation is due to ischemia or merely to a different electrode position. Some cardiologists even routinely ignore the results of certain electrode leads that are frequently misplaced, such as V3, which actually provides one of the key views of the heart. Standardization of measurement conditions is therefore critical to the usefulness of this important diagnostic tool and represents a long-felt need in the field for an easily applied, clinically practical device to solve this problem.

The need for manual placement of each electrode has other effects on the usefulness and efficiency of the EKG test. Among other things, placement of the electrodes takes a considerable amount of time, often constituting the rate-limiting step in obtaining the tracing. One estimate is that it takes on average seven minutes to place the six precordial leads for a standard EKG test. Since the average 250 bed hospital may do over 100 EKG tests per day, a lot of technician time is consumed by doing this repetitive task, time that could be beneficially devoted to other activities. This waste of time is particularly apparent in a hospital situation where the same patient will often have multiple EKG tests done in a short period of time. On average a cardiac patient admitted for four days will have at least seven EKGs (more often than not, greater than ten), and each time the electrodes must be manually repositioned. Time is also consumed, of course, each time an EKG must be repeated due to poor electrode placement, and this loss is further compounded by the fact that the cost of the repeat test may not be billable to the patient's insurance provider because it was required due to the hospital's error.

Another problem frequently encountered during the administration of an EKG test utilizing conventional precordial electrodes is that the self-adhesive disposable "stickies" with which the precordial electrodes are generally manually applied are good for only one test administration and are easily dislodged and/or ruined. This means that replacements are frequently required, often up to several per patient per test. This can add up over time to a significant expense for the hospital, an expense that often cannot be passed through to the patient's insurance provider. Similar problems with electrode dislodgement occur when suction cups are used to apply the electrodes, particularly where the patient has large pectoral muscles or breasts, has a hairy chest, is sweaty, or the test is performed with the patient partially or completely sitting up. Other problems with the current method of EKG electrode placement include the difficulty in, and time required for, cleaning the electrodes and/or suction cups between patients, and the potential for entanglement, or even misconnection, of the individual electrode wires. The latter problem is particularly significant because each electrode must be connected to a specific wire that in turn must be connected to a specific input on the EKG machine or the tracing obtained will not be accurate.

Although the prior art teaches several approaches to solving various of the above-described problems that have long been encountered with the conventional twelve-lead EKG electrode system, none of the systems described allow complete freedom and guidance for the accurate and independent positioning and attachment of all six precordial electrodes when the test is initially performed on a particular patient, in conjunction with complete reproducibility of results for all future EKGs on that patient without the need for individual repositioning of the electrodes each time the test is performed. For example, in Rollman et al., U.S. Pat. No. 5,370,116, three of the precordial electrodes are completely fixed on a platform, while the other three are independently moveable but attached via leads rather than being resident on the platform. Therefore, although allowing some freedom of adjustment of electrode position, Rollman et al. do not teach an apparatus or method that allows all electrodes to be independently positioned during the first use and then be locked into that position to ensure consistent reproducibility of future test results.

Similarly, in Rubin, U.S. Pat. No. 4,854,323, all six precordial electrodes are independently positionable along a platform, after which each is held in place on the platform by a clip. However, the electrodes of Rubin cannot be locked into place in a permanent manner, as the clips may be easily jarred and dislodged or even be subject to accidental or deliberate tampering. Further, the platform of Rubin is necessarily made of a semi-rigid material that will hold the shape into which it is bent, otherwise the electrodes cannot be properly positioned on the patient's torso. Besides the fact that this design provides no guidance to the technician for the proper positioning of the electrodes, the need to use a semi-rigid material for the platform creates a serious drawback in that the platform is not able to properly accommodate patient movement or respiration without loss of electrical contact. This problem in turn may lead to seriously inconsistent EKG test results. What has been needed, therefore, is a completely reusable and accurate patient-specific EKG electrode system that must be fitted to a particular patient only once, after which the system may be consistently, accurately and repeatedly reused for that patient without remeasurement or precordial electrode repositioning.

OBJECTS OF THE INVENTION

Accordingly, a primary object of the present invention is to provide an easy-to-use way to consistently map and measure cardiac function.

In particular, an object of the present invention is to provide a way to reliably and consistently map and measure the cardiac function of a particular patient at any number of spaced time intervals.

A further particular object of this invention is to provide a way to quickly and accurately map and measure the cardiac function of any patient.

Another particular object of this invention is to provide a patient-specific EKG electrode set that may be reliably and conveniently reused any number of times to provide consistently reproducible measurements for a particular patient.

An additional particular object of the invention is to provide a set of EKG electrodes that may be quickly and easily attached to any patient in the proper positions.

A further particular object of this invention is to provide an easy-to-use and consistently positionable electrode system that can be used for either left- or right-sided operation.

Additionally, it is desired to have a flexible electrode platform that can be used for both EKG testing and the delivery of therapeutic electrical impulses.

SUMMARY

A patient-specific EKG electrode platform and positioning system allows the standard twelve-lead EKG test to be performed in a more accurate, consistent, and reproducible manner by eliminating individual positioning of the six precordial electrodes for all but the first test on a particular patient. A platform for mounting and positioning electrodes is configured to allow the precordial electrodes to be aligned in the optimum manner for the performance of the EKG test. Each of the six precordial electrodes V1–V6 is mounted on the platform via a moveable mount slidably attached to the platform.

After the platform has been properly aligned on the torso of the patient, the mount containing each electrode is moved until it is properly positioned for the test. The position of each electrode and its respective mount is then permanently fixed utilizing a lock-down mechanism that can also serve to create a connection between the electrode and a wire lead connectable to the EKG machine. All six precordial electrodes are thereafter accurately and permanently positioned on the platform so that when the platform is subsequently aligned properly on a particular patient's torso, all six electrodes will be properly and consistently positioned for a repeat administration of the EKG test on that patient without need for readjustment of the individual electrodes. The now patient-specific platform may be aligned properly on the patient during subsequent tests by utilizing an index marker that was marked or physically shortened during the initial alignment of the platform to match up with a selected anatomical reference point.

This same platform may be simultaneously or sequentially used for delivering appropriate energy to the heart for external pacemaker therapy, cardioversion of tachydysrhythmias, and emergency defibrillation, since the platform is in the proper position for transmitting current to each of the six precordial electrodes. This will eliminate one of the time wasting steps in ACLS: delivering the shock, removing the paddles and awaiting the monitor to recapture the signals.

Changing the orientation of the delivery electrodes or paddles can decrease the level of energy delivered to the patient, while sending such shocks in a manner that more likely will surround the fibrillatory impulses. The platform of the present invention will deliver the therapeutic shock in a more physiological orientation than the current point A to point B methodology. Because each individual is different, the platform can be manipulated to align properly on any patient. The consistent cardiogram platform enables the current to flow from several precordial positions, paralleling the major vectors of signal impulse as reflected on the EKG.

The present invention can also improve the manner in which therapeutic electrical impulses are delivered. Typically the energy is sent to the patient simultaneously through two electrodes. The underlying heart cells are in various stages of refractoriness. Since the platform of the present invention has electrodes located near the SA node, the AV node, parallel to the bundle of His, and the left/right bundle branches, it is reasonable to deliver therapeutic electrical stimulation sequentially through the electrodes instead of simultaneously, thus facilitating a more physiologic cardiac response. Therefore, in addition to sending the signal simultaneously through all the electrodes, the therapeutic electrical impulses can alternatively be delivered sequentially delayed from V1 and V2 to V3 to V4 through V6 in a manner that simulates the temporal sequence of the normally functioning heart. Either way, the platform of the present invention focuses the impulse to several points of the heart in a more targeted and precise manner. This is termed herein "asynchronous defibrillation," which is a component of the general concept known as "asynchronous therapeutic electrostimulation" as it applies to tachydysrhythmias and bradydysrhythmias.

The phrase "asynchronous defibrillation" includes sequentially delivering therapeutic electrical stimulation in addition to utilizing the present methodology of simultaneous electrical stimulation. The platform of the present invention offers a larger enveloping electrode zone around the fibrillatory area. Using integrated software, the strength of the fibrillatory waves within each electrode coverage area can be interpreted. Subsequently, and simultaneously or sequentially, therapeutic impulses would be sent at specifically tailored energy levels and tailored energy burst times through each electrode. The level of energy sent would be sufficient to overcome the fibrillation, but compared to the global high energy approach currently delivered through the 2 lead system, the levels used could be lower, thus reducing burns, discomfort, and myocardial injury.

The same rationale would apply to pacemaker therapy. It is well known that capture and propagation of a signal by the underlying heart is critical to successfully establishing an appropriate heart rate transcutaneously. The energy requirement to effectively pace a heart through the existing 2-electrode technology often is very uncomfortable for the patient. The platform array could take advantage of the same physiological considerations in cardiac pacing as in cardioversion, since altering the location of the electrodes to a more physiologic orientation may allow lower energy to achieve the same results. The asynchronous timing option may offer an advantage of paralleling the normal physiologic impulse propagation of the heart.

The present invention offers a significant improvement on the monitoring and treatment of the cardiac patient, especially the sudden cardiac death victim, and patients with symptomatic brady-dysrhythmias and tachy-dysrhythmias.

In a preferred embodiment of the invention, a flexible plastic precordial electrode platform has a "reversed S" shape and embedded wires accessible at one end of the platform for connection to the EKG machine and to a source of electrical impulses. The precordial electrodes V1–V6 are mounted on the undersides of plastic electrical connectors that are mounted around the precordial electrode platform in a manner that allows each electrode to initially be freely moveable horizontally along the length of a section of the platform. Once each electrode is properly positioned, the electrical connector on which it is mounted is activated by compressing the plastic connector body around the platform, simultaneously fixing the electrode in place and making an electrical connection between the electrode and two of the embedded wires.

It is normally desirable to utilize one or more limb electrodes in conjunction with the precordial electrode platform, and any of a number of standard implementations may be used. A cabling device may be employed as a convenient method of connecting the precordial electrode platform, and possibly the limb electrodes, to the EKG machine. A further option is the inclusion of standard telemetry devices on each connector to transmit signals to the EKG machine or some other measurement device, either instead of or simultaneously with transmission of signals through the regular electrode wiring, the latter allowing both the standard telemetry test and the 12-lead EKG to be taken at the same time with the same device. This embodiment of the invention may also be easily configured for use in a right-sided EKG test by reversing the platform horizontally, flipping over the connectors, and replacing the connectors on the platform so that each electrode is again in contact with the torso of the patient.

In an alternate embodiment of the invention, the totally integrated precordial electrode platform has multiple articulating or telescoping arms, particularly adapted for folding or collapsing the device for transport and storage. The electrodes are independently mounted via mounting pads on the movably connected arms and each may be freely adjusted along its respective arm until it reaches the proper alignment, after which it is fixed into the proper position by serrations, teeth, or other ridge-like protrusions present along the surface of each arm.

In an additional embodiment of the invention, the patient retains the patient-specific device after initial setup in a carrying case that holds the device, various optional accessories, and relevant informational materials. In the preferred embodiment, the case is made from molded plastic, having a built-in carrying handle. The carrying case has a well shaped and sized to hold the precordial electrode platform of the invention without damage to the wires or electrode mounts, with one or more additional wells optionally provided to hold various optional accessories, such as a set of limb electrodes or a cabling device. The case may optionally also hold informational accessories and materials, such as a base-line EKG tracing for the patient taken using the patient-specific precordial electrode platform, a Patient Information card, disease management pamphlets or records, and instructional materials for use of the electrode platform.

The method of cardiac mapping and measurement utilizing the electrode positioning device of the present invention begins with proper alignment of the precordial electrode platform on the patient. The alignment is permanently adjusted by marking or altering the index device and each electrode is then properly positioned and locked into place. The four limb leads are next attached to the patient, and the leads from the precordial electrodes and limb leads are all connected to the EKG and source of electrical energy. The EKG test and delivery of therapeutic electrical impulses are performed in the normal manner, after which the electrode leads are disconnected from the machines and the limb electrodes and precordial electrode platform are removed from the patient and saved for future use. For subsequent administration of the EKG test and delivery of therapeutic electrical impulses, except for simple alignment of the precordial electrode platform previously setup for the patient on that patient, no adjustment of electrode position is necessary, with the technician proceeding straight to attachment of the limb leads, followed by connection of the leads to the machine and performance of the procedures. A completely accurate and consistently reproducible EKG result and delivery of electrical impulses to targeted spots are therefore obtained with minimal setup time.

BRIEF DESCRIPTION OF THE DRAWINGS

FIG. 2b is an enlarged reverse view of the electrode assembly of the embodiment of FIG. 2a;

FIGS. 6a and 6b are block diagrams of one embodiment of the method of cardiac mapping and measurement using the apparatus of the present invention, FIG. 6a illustrating the initial use of the invention for a particular patient and FIG. 6b illustrating subsequent uses for that same patient.

DETAILED DESCRIPTION OF THE PREFERRED EMBODIMENT

The present invention allows the standard twelve-lead EKG test to be performed in a more accurate, consistent, and reproducible manner for any particular patient by requiring that the six precordial electrodes be individually positioned only for the first time the test is ever performed on the patient. The invention guides the initial electrode positioning to ensure that it is correct, and then allows the electrodes to be permanently locked into place on a reusable platform that is thereafter perfectly configured for EKG tests on that particular patient.

The present invention also allows the same electrodes to be used for the delivery of therapeutic electrical impulses to the patient, allowing virtual simultaneous acquisition of EKG signals from the electrodes and delivery of current to the electrodes. Throughout the description below, the platform is described primarily with respect to its applicability to EKG testing. It is to be appreciated that the description below applies to use of the platform to deliver electrical impulses to the heart for external pacemaker therapy, cardioversion of tachydysrhythmias, and emergency defibrillation as well.

Figure 1:
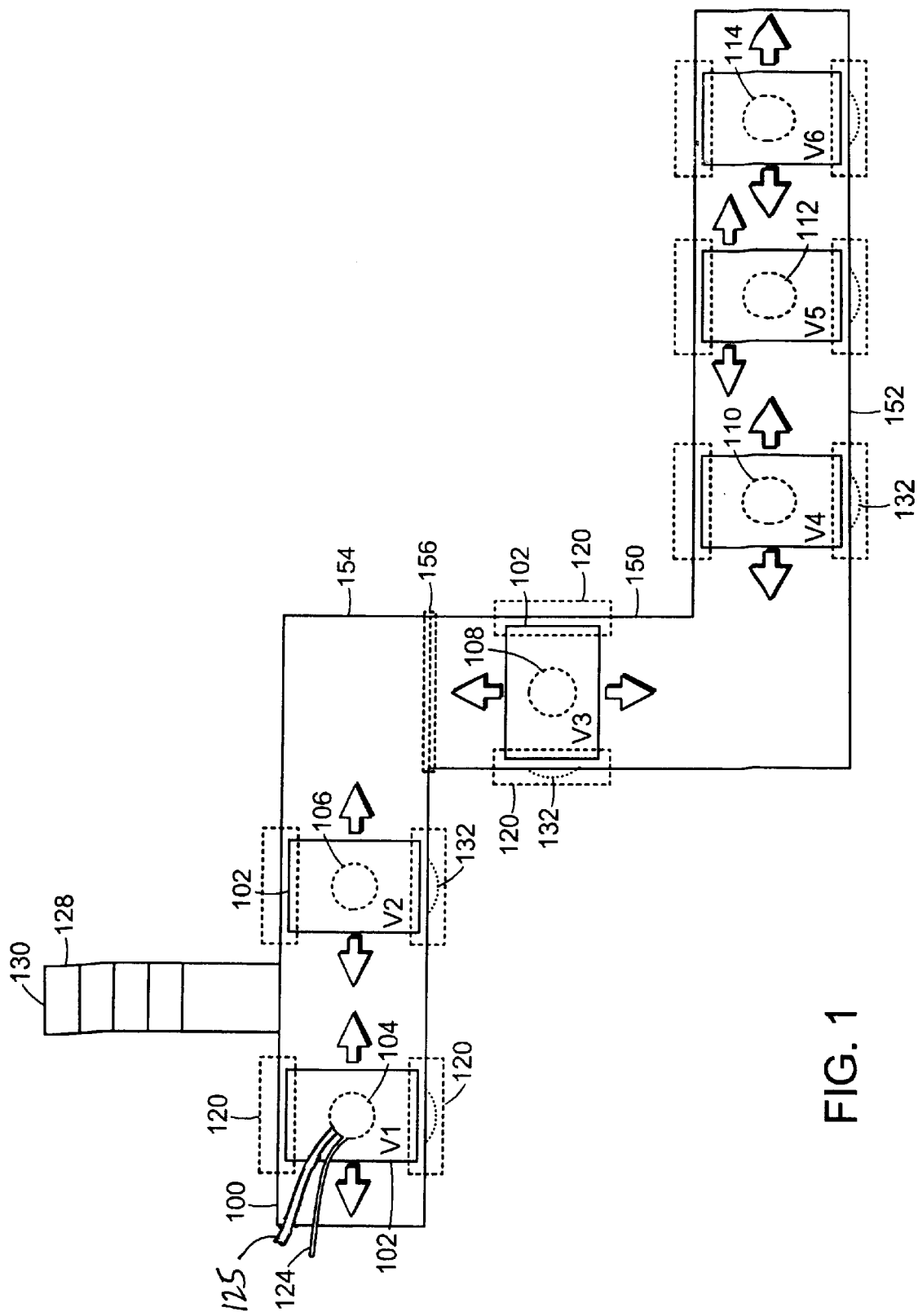
FIG. 1 is a block diagram of one implementation of the patient-specific precordial electrode platform of the present invention.

As seen in the block diagram of an embodiment of the invention shown in FIG. 1, a platform 100 for mounting and positioning electrodes is substantially flat and shaped in a manner that allows the electrodes to be aligned in the optimum manner for the performance of the EKG test and delivery of therapeutic electrical impulses. While the preferred embodiment of the platform 100 of the invention is optimally designed for positioning of the precordial electrodes utilized in the standard twelve-lead EKG test, the invention may in fact be used for any type of test requiring precise positioning of multiple electrodes and may be configured in any alternate manner convenient for that test. In a preferred embodiment of the invention, the platform has a material composition and a configuration that allow the device to be collapsed or folded for storage.

The flat shape of the platform in the preferred embodiment is designed to allow the platform to conform to the torso of the patient, but clearly any shape that would bring the electrodes into the optimum position for the test would also be suitable. As the invention is shown in FIG. 1, the platform has the preferred "reversed S" shape that allows optimum alignment of the electrodes for the standard twelve-lead EKG test. Again, this is only one configuration of the invention contemplated by the inventor; many other configurations also allow the electrodes to be properly positioned on the torso of the patient and could therefore be used in place of the "reversed S" configuration shown. In a preferred embodiment, the configuration utilized accommodates simultaneous use of defibrillation devices.

Mounted on the precordial electrode platform 100, as the invention is implemented in the embodiment of FIG. 1, are the six precordial electrodes V1–V6 that are utilized in performance of the standard twelve-lead EKG test. In this embodiment, each electrode is positioned on a moveable electrode mount 102 that is slidably attached to the electrode platform 100. Although the preferred embodiment utilizes a slidable mount to contain each electrode, any other type of positioning and mounting device know in the art would also be suitable. As shown in FIG. 1, each electrode mount 102 is freely moveable in a horizontal manner within a specific range on the platform 100. Alternate embodiments of the invention might alternatively have mounts that are moveable in a vertical manner or possibly even freely moveable within a specified range. The invention contemplates the incorporation into the electrode mounts 102 of any of the large variety of EKG electrodes commonly available and used in the art or their equivalents, for example any of the standard disk electrodes offered by such companies as In Vivo Metric, ConMed Corporation, Bio-Detek Incorporated, Kendall LTP, Clinical Devices, Inc., Hewlett-Packard, and Vermont Medical, Inc.

The V1 electrode 104 of the standard twelve-lead EKG is shown positioned on the left-most electrode mount 102. The electrode 104 is positioned in the mount 102 with respect to the platform 100 in a manner that allows the electrode 104 to contact the skin of the patient. This may be accomplished by any number of methods well-known in the art, such as by providing a slot in the platform 100 and positioning the electrode on the underside of the mount 102 so that it extends through the slot to contact the patient or by having the mount 102 extend around the platform 100 with the electrode mounted downward on the bottom of the mount. Standard electrode conducting gel may of course be employed with this invention. In the preferred embodiment, the platform 100 and mounts 102 are constructed from easily washable and reusable materials to facilitate post-test clean-up of the device.

After the platform 100 has been properly aligned on the torso of the patient, mount 102 containing electrode V1 104 is moved horizontally until it is positioned just to the immediate right of the patient's sternum. The position of electrode V1 104 and its respective mount 102 are then locked into place utilizing a lock-down mechanism 120 that can take the form of a clamp or any other suitable mechanism known in the art. If electrode V1 104 is not already connected to a wire lead 124 that is connectable to the EKG machine, then ideally connection will also be made to such a wire at the time that the lock-down mechanism is activated. Electrode V1 104 is also connected to a wire lead 424 that is connectable to a source of electrical energy, e.g., a defibrillation machine. One possible implementation of this type of connection is described in more detail in conjunction with FIG. 2b.

Similarly, electrode V2 106 is positioned by horizontally sliding its mount 102 until electrode V2 106 is just to the left of the patient's sternum. Electrode V2 106 and its mount 102 are then locked onto place with another lock-down mechanism 120. Electrode V4 110 is positioned and locked into place at the midclavicular line, electrode V5 112 at the anterior axillary line, and electrode V6 114 at the midaxillary line. Finally, electrode V3 108 is positioned and locked in halfway between electrodes V2 106 and V4 110. All six electrodes are now accurately and permanently positioned on the platform 100 so that, whenever the platform 100 is subsequently aligned properly on the particular patient's torso, the electrodes will be properly and consistently positioned for a repeat administration of the EKG test on that patient and the delivery of therapeutic electrical impulses without any need for readjustment of any of the individual electrodes.

The platform 100 is initially aligned so that electrodes V1 104 and V2 106 fall in the fourth intercostal space and electrodes V4 110, V5 112, and V6 114 fall in the fifth intercostal space. Platform 100 may optionally include a vertical section adjustment 156 for lengthening or shortening the vertical arm or section 150 of platform 100 that allows the position of upper horizontal arm or section 154 to be adjusted vertically with respect to lower horizontal arm or section 152, thus allowing electrodes V1 104, V2 106, V4 110, V5 112, and V6 114 to lie in their correct respective intercostal spaces. Although vertical section adjustment 156 is shown in FIG. 1 to lie between upper horizontal section 154 and vertical section 150, it could be located between vertical section 150 and lower horizontal arm 152 with equal functionality. For quick use in emergency situations, the platform 100 may be pre-packaged in a pre-configured state such that the starting locations of electrodes V1 –V6 are the proper locations of those electrodes for the ninetieth percentile (90%) of the target (adult male, adult female, or pediatric) population.

For subsequent uses, the now patient-specific platform 100 is aligned properly on the patient by using an index marker 128. When the platform 100 is aligned initially, index marker 128 is either marked or physically shortened so that, when the top 130 of the marker 128 is aligned with a particular anatomical reference point, the platform 100 will be properly aligned. In the preferred embodiment of the invention, either the jugular notch (the indentation above the sternum midline), the angle of Louis, or the xiphoid process (posterior and lowest division of the sternum) is used as the anatomical reference, but any consistently locatable anatomical reference point would be suitable.

Once the platform 100 is properly aligned on the patient, it may be helpful to be able to more firmly attach it to the patient to prevent it being accidentally dislodged by patient movement or breathing or by the actions of medical personnel. If this is desired, some form of attachment device or substance 132 may be provided, either surrounding the individual electrodes or in any other convenient position on the platform 100. Any type of the many attachment methods known in the art would be suitable, such as suction cups, sticky or "surgi" tape, straps around the patient, weights, etc., but in the preferred embodiment a water-resistant reusable adhesive substance (e.g. Wet-Stick™) incorporated onto the back of platform 100, preferably having an easy-to-use peel-off backing, is employed.

Since platform 100 has six precordial electrodes through which electrical energy can be transmitted, as opposed to the conventional two paddles, the level of energy delivered to the patient can be decreased, and the precise positioning of the electrodes also allows for transmission of shocks in a manner that more likely will surround the fibrillatory impulses. Thus, platform 100 will deliver the therapeutic shock to the precordial electrodes in a more physiological orientation than the current point A to point B methodology. Thus, the current flows to several precordial positions, paralleling the major vectors of signal impulse as reflected on the EKG. Specifically, because precordial electrodes are located near the SA node, the AV node, parallel to the bundle of His, and the left/right bundle branches, it is reasonable to deliver therapeutic electrical stimulation sequentially through the electrodes instead of simultaneously, thus facilitating a more physiologic cardiac response. Therefore, in addition to sending the signal simultaneously through all the electrodes, the therapeutic electrical impulses can also be delivered sequentially delayed from V1 and V2 to V3 to V4 through V6 in a manner that simulates the temporal sequence of the normally functioning heart. Thus, whether the signals are transmitted simultaneously to each electrode, or in a desired sequence, the electrical impulses are focused on several points of the heart in a more targeted and precise manner, denoted herein as "asynchronous defibrillation." Asynchronous defibrillation is a component of the general concept asynchronous therapeutic electrostimulation as it applies to tachydysrhythmias and bradydysrhythmias.

Asynchronous defibrillation includes sequentially delivering therapeutic electrical stimulation in addition to utilizing the present methodology of simultaneous electrical stimulation. The consistent cardiogram platform offers a larger enveloping electrode zone around the fibrillatory area. Using integrated software we can interpret the strength of the fibrillatory waves within each electrode coverage area. Subsequently, and simultaneously or sequentially, therapeutic impulses would be sent at specifically tailored energy levels and tailored energy burst times through each electrode. The level of energy sent would be sufficient to overcome the fibrillation, but compared to the global high energy approach currently delivered through the 2 lead system, the levels used could be lower, thus reducing burns, discomfort, and myocardial injury.

This same rationale applies as well to pacemaker therapy. It is well known that capture and propagation of signal by the underlying heart is critical to successfully establishing an appropriate heart rate transcutaneously. The energy requirement to effectively pace a heart through the existing 2-electrode technology often is very uncomfortable for the patient. The platform array could take advantage of the same physiological considerations in cardiac pacing as in cardioversion, altering the location of the electrodes to a more physiologic orientation may allow lower energy to achieve the same results. The asynchronous timing option may offer an advantage of paralleling the normal physiologic impulse propagation of the heart. Thus, the device of the present invention offers a significant improvement on the monitoring and treatment of the cardiac patient, especially the sudden cardiac death victim, and patients with symptomatic brady-dysrhythmias and tachy-dysrhythmias.

Another advantage of the present invention is that, in addition to allowing the simultaneous use of the electrodes for acquiring an EKG or telemetry signal and delivery of therapeutic electrical impulses such as defibrillator shocks, the platform allows healthcare personnel to also apply chest compressions and perform CPR. Such simultaneous performance can shorten the delivery time of these various procedures, thereby improving the chances of successfully providing emergency cardiac care.

While the intent of the invention is to provide a patient-specific precordial electrode platform with electrodes that are permanently fixed in the proper location for the specific patient, it is recognized that factors such as the patient's anatomy may change radically over time, such as, for example, where the patient puts on or loses a lot of weight. It is contemplated, therefore that the properly positioned precordial electrodes may, under specific circumstances, be repositioned on the platform. Removal of the electrodes for repositioning requires either a specific tool or special knowledge about the operation of the device, in order to ensure that the electrode mounts may not be accidentally or deliberately removed and/or repositioned by the patient or other non-trained individual.

Figure 2A:
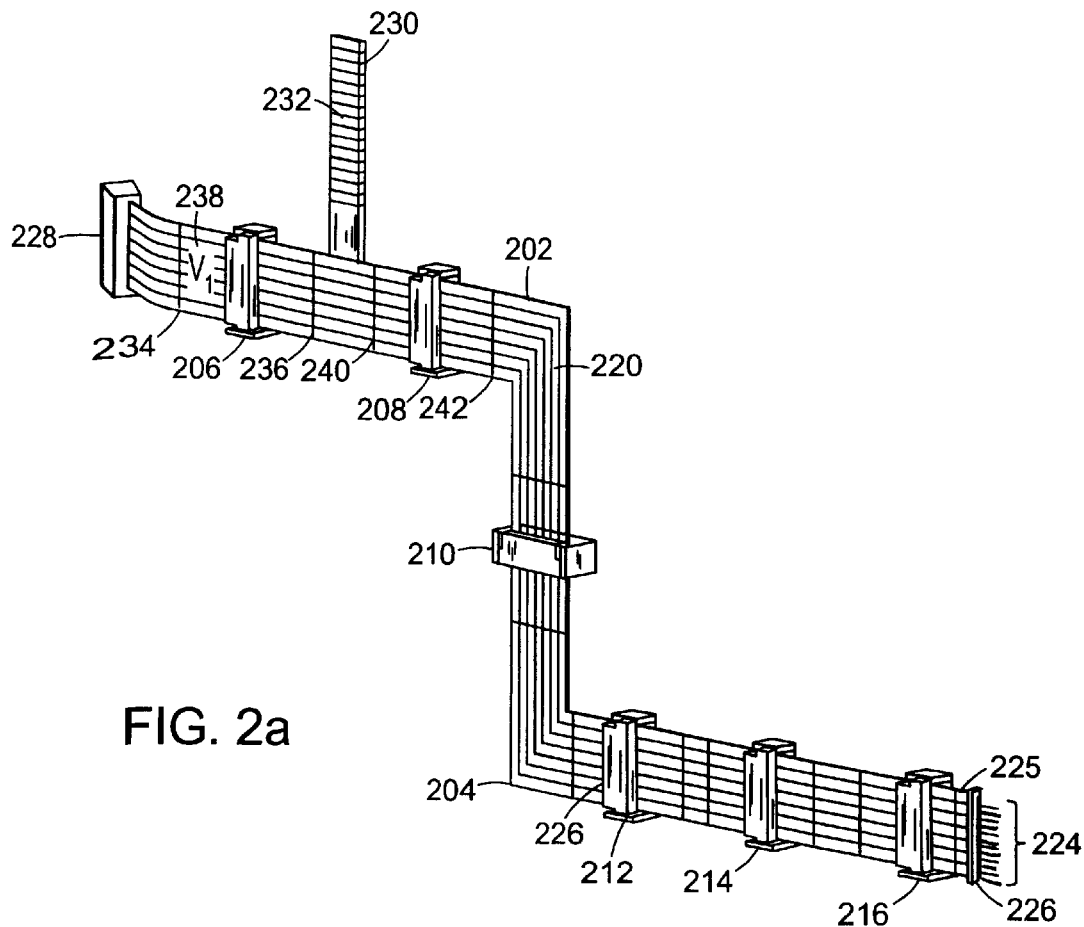
FIG. 2a is a representation of a particular embodiment of the patient-specific precordial electrode system of the present invention.

A preferred embodiment of the invention is shown in FIG. 2a. A flexible lightweight plastic precordial electrode platform 202, having embedded wires 220, has a "reversed S" shape 204 for optimum positioning of the precordial electrodes. The embedded wires 220 are accessible at the electrically active end 225, which may be left as a bare end or bare wires or be connected to a cap 226 from which wire leads 224 emerge that are connectable to the EKG machine and the source of electrical energy via alligator clips, universal clips, or any other connection method commonly known in the art. In the embodiment illustrated, the other end of platform 202 is dead-capped 228 or smoothly finished, but it may be left electrically active if alternate uses of the device are contemplated. The flexible nature of the platform 202 has the advantage of allowing the device to be rolled up for storage if desired.

The precordial electrodes V1–V6 are mounted on the undersides of plastic electrical connectors 206, 208, 210, 212, 214, and 216 respectively. Electrical connectors 206, 208, 210, 212, 214 and 216 are preferably made of plastic and are mounted around precordial electrode platform 202 in a manner that allows each to initially be freely moveable horizontally along the length of a section of the platform 202. As described in more detail in conjunction with FIG. 2b, once each electrode is properly positioned, the electrical connector on which it is mounted is activated by compressing the plastic connector body around the platform 202, simultaneously fixing the electrode in place and making an electrical connection between the electrode and the appropriate pair of the embedded wires 220, such that the electrode can be connected to the EKG machine and the source of electrical energy. In the preferred embodiment, the platform 202 and precordial electrodes are then maintained in contact with the patient's torso by use of a preferably reusable and waterproof adhesive located on the underside of electrical connectors 206, 208, 210, 212, 214 and 216 and surrounding each of the six precordial electrodes V1–V6. Alternatively, the adhesive material could be located directly on the platform 202 itself.

In the preferred embodiment of FIG. 2a, the platform 202 is properly aligned on the torso of the patient using index marker 230. Initially, the platform 202 is adjusted so that electrodes V1 and V2 are within the fourth intercostal space and V4, V5, and V6 are within the fifth intercostal space. As described in conjunction with FIG. 1, platform 202 may be configured so that the height of the vertical portion may be adjusted to allow the electrodes V1, V2, V4, V5 and V6 to properly lie in the correct intercostal spaces. In a preferred embodiment with this optional feature, the vertical arm of platform 202 is solidly connected to only one of the two horizontal arms. At its other end, the vertical arm is initially connected to the other horizontal arm solely by extensions of the embedded wires 220. The vertical arm is configured so that it slightly narrows at this end, allowing the arm to be slid within a sleeve provided on the corresponding horizontal arm. Once the proper length of the vertical arm is determined, the sleeve provided on the horizontal arm is permanently clipped, locked or fastened around the vertical arm narrow end using any of the myriad fastening techniques know in the art, thus permanently maintaining the vertical arm at that specific length and hence also permanently maintaining the specific distance of separation between the two horizontal arms.

Next, a consistent anatomical reference is selected on the patient's anatomy, generally the jugular notch or perhaps the angle of Louis. The index marker 230 is then adjusted or marked so that, when it is placed at the reference point, the precordial electrode platform is properly aligned on the torso of the patient. In a preferred embodiment, the index marker 230 is plastic that is provided with multiple tear points 232, allowing the length of the marker to be precisely conformed to the distance between the selected anatomical reference point and the proper position of the platform 202 by simply tearing off the unneeded portion of the marker 230.

In the embodiment of FIG. 2a, the platform 202 is provided with optional imprinted markings that guide the position of each electrode. As shown in FIG. 2a, marks 234 and 236 delimit the area within which electrode V1 should be positioned, indicated on the platform by the label "V1" 238. Similarly, marks 240 and 242 delimit the area within which electrode V2 should be positioned. If desired, additional location information may be imprinted on the platform within these spaces, such as, for example, "V1: fourth intercostal space, right of sternum".

Figure 2B:
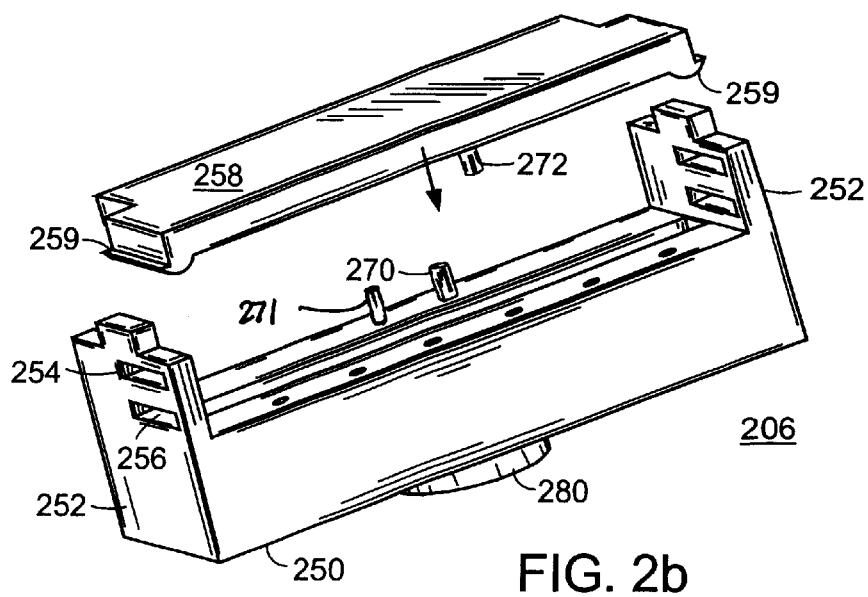

A preferred embodiment of the "snap-down" electrical connector 206, 208, 210, 212, 214, and 216 is shown in FIG. 2b. Similar in concept to the electrical contact and connector taught in U.S. Pat. No. 3,990,767 (Narozny, 1976), the connector 206 of the present invention has an electrically connective bottom portion 250 that extends into two side pieces 252. Each side piece 252 has an upper slot 254 and a lower slot 256. A moveable top piece 258 having two tabs 259 is loosely installed between the two side pieces 252, initially resting in the upper slot 254 of each side piece 252. On the top of the bottom portion 250 and the bottom of the top piece 258 are lower 270, 271 and upper 272 electrical contacts respectively.

The electrode 280 is positioned on the underside of the bottom portion 250 of the connector 206. Lower electrical contacts 270, 271 are in contact with the electrode 280, and the lower 270, 271 and upper 272 contacts are positioned over the particular embedded wires 220 in the platform 202 that is designated to carry signals received by that particular electrode (V1–V6) to the EKG machine and from the source of electrical energy. When the connector is activated by being compressed ("snapped-down") around the platform 202, upper portion 258 moves downward until the tabs 259 come to rest in the lower slots 256 in the connector sides 252. This causes the upper 272 and lower 270, 271 electrical contacts to impale platform 202 and make an electrical connection with the pre-specified embedded wires 220. In the preferred embodiment shown in FIG. 2b, only the lower contacts 270, 271 are electrically active, but use of the upper contacts 272 for one or more functions is also contemplated, as discussed further in conjunction with FIG. 3. Even when not electrically active, upper contact 272 provides further stability to the position of the locked-down connector 206 on the platform 202.

Figure 3:
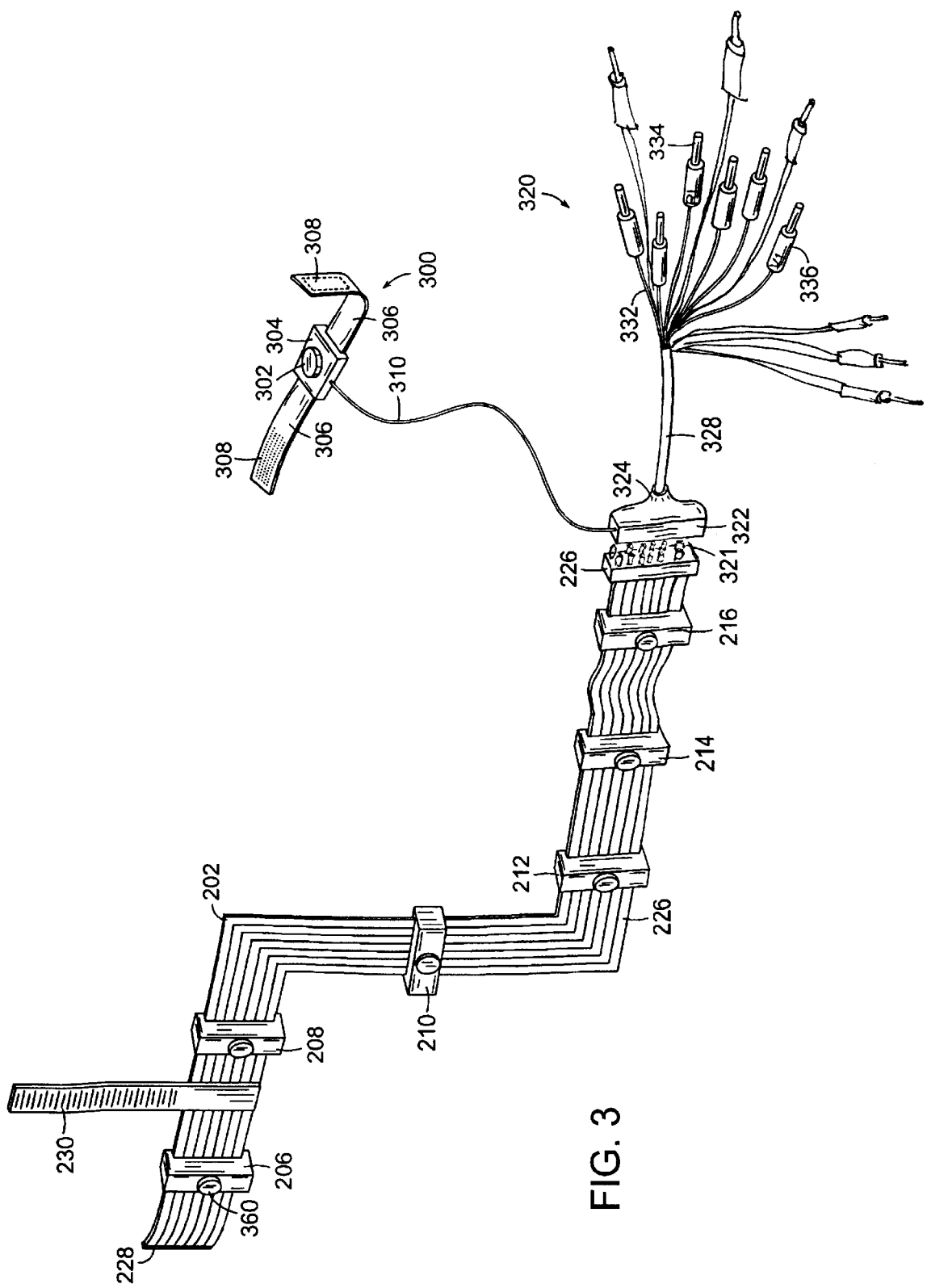
FIG. 3 is a representation of the embodiment of FIG. 2a showing the optional telemetry, electrode lead cable, and limb electrode features.

Various optional additions to the preferred embodiment of FIG. 2a are illustrated in FIG. 3. In most circumstances, it will be desirable to utilize one or more limb, or extremity, electrodes in conjunction with the precordial electrode platform 202. For the standard twelve-lead EKG test, an electrode is placed on each of the patient's arms and legs. A preferred embodiment of an adjustable limb electrode 300 is shown in FIG. 3, having an electrode 302 mounted on or in a mounting pad 304. The electrode 302 will preferably be of the same type used on the precordial electrode platform 202, but can be an alternate type if needed or desired. The mounting pad may be foam or any other convenient and preferably comfortable type of material, and may even for consistency in the appearance and operation of the electrode system be the type of electrode mount 206 shown in FIG. 2b.

In the preferred embodiment of FIG. 3, the mounting pad 304 is held around the limb via adjustable straps 306 having Velcro® ends 308, but any form of elastic, cloth, leather, bendable plastic or other bracelet-like adjustable platform, attached by any form of connector such as Velcro®, buckles, snaps, buttons, or ties, would be suitable. The four limb electrode assemblies used, for example, in the twelve-lead resting EKG test, may be individually color-coded for both quick identification and to aid in avoiding connection to the wrong limb. The electrode is then connected via a wire lead 310 either to the platform 202, or directly to the EKG machine, or, alternatively, through a cabling device 320 to the EKG machine.

Use of a cabling device 320 is an alternate method of connecting the precordial electrode platform 202, and possibly the limb electrodes 300, to the EKG machine and to the source of electrical energy. For this option, the cap 226 is topped with prongs 321 that fit into connector 322, making individual electrical connections to cable wires 324. Additional wire leads may enter the cable at this point, such as wire lead 310 from limb electrode 300. Cable wires 324 are preferably covered by a sheath 328 that serves to simultaneously protect the wires, shield the signals carried on the wires from interference, keep the wires together, and prevent entanglement of the wires with each other or with persons or other equipment, although wires 324 may be left uncovered if desirable for some particular application. At the EKG machine and source of electrical energy, the wires emerge again from the sheath 328. Each individual wire 224 may be left bare, for connection to the EKG machine and source of electrical energy via alligator clips or any other method known in the art, or each individual wire 332 may end in a plug 334, optimally labeled 336 with the name of the electrode to which it is connected, e.g., "V1" or "RL" (right leg). Plugs 334 may be banana-type plugs or any other similar type pf connector known in the art.

Another option to the embodiment of FIG. 2a is the inclusion of built-in telemetry devices. Telemetry devices may be used to send signals either to the EKG machine, as might be particularly useful during a stress-testing situation, or to some other measurement, storage, or display device. Any of the EKG telemetry devices commonly available or known in the art, or their equivalents, are suitable, such as those offered by Hewlett-Packard or 3M Corporation. The invention may alternatively be optionally configured without built-in telemetry devices, but with a built-in ability to interface with telemetry equipment and/or telemetric communications devices. The telemetry devices can be configured and used to obtain the twelve-lead resting EKG measurements or for performance of any of the other standard telemetry-based tests (MCL, II, etc.).

As shown in FIG. 3, individual telemetry devices 360, e.g. telemetric male connectors, may be mounted on the top of each connector 206, 208, 210, 212, 214, and 216 to create a multi-function device. Each telemetry device 360 transmits the signals received from its associated electrode and enables a different physical acquisition configuration.

In the preferred embodiment, the signals are received by the telemetry device 360 from the electrode via the upper electrical connector 272 that is located on the bottom of the upper portion 258 of the connector and placed in contact with the signals from the electrode via the electrical contact with the embedded wire 220 formed when the connector is activated. If extremity electrodes 300 are being used, a telemetry device 360 may also be placed on the upper side of each electrode mounting pad or connector 304, either alone or, if desired, in electrical contact with the respective conventional electrode. If required by the application, a separate ground electrode may be attached either on the platform or between the platform and a suitable spot on the patient's body via a wire lead. The telemetry devices 360 may be used either alone or in conjunction with wire lead connection 224 to the EKG machine.

Figure 4:
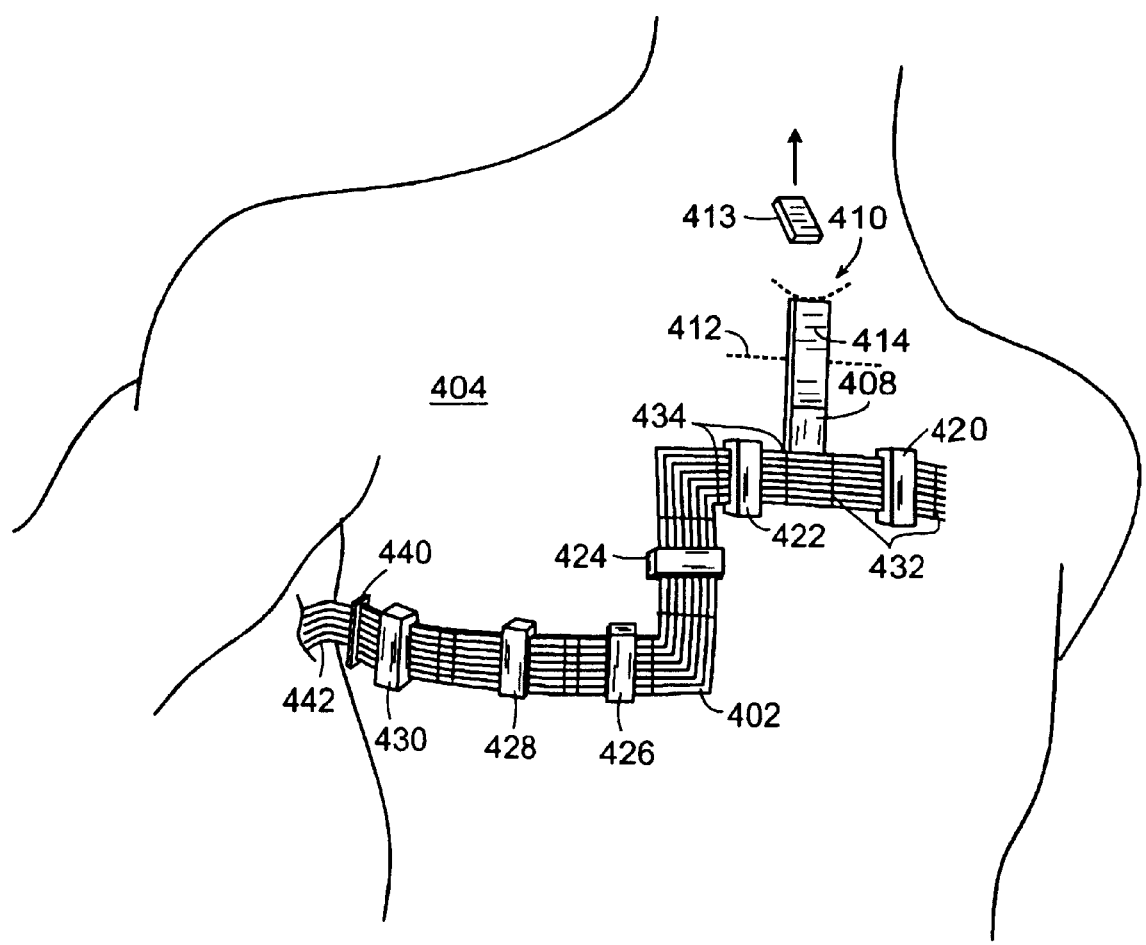
FIG. 4 is a representation of the embodiment of FIG. 2a after reconfiguration for right-sided operation, shown in place on a human torso.

The preferred embodiment of the invention may also be easily configured for use in a right-sided EKG test (as opposed to the left-sided operation for which the embodiment of FIG. 2a is configured). FIG. 4 illustrates the embodiment of the precordial electrode platform of FIG. 2a on a human torso 404 after reconfiguration for right-sided operation. Before initial alignment on the torso 404, the platform 402 is reversed horizontally so that it now forms a "forward S" configuration. The connectors 420, 422, 424, 426, 428, and 430 with their associated electrodes are removed from the platform by removal of the top piece 258 of each connector. Each connector 420, 422, 424, 426, 428, and 430 is flipped over and then replaced on the platform 402 so that each electrode returns to the underside of the platform and is again in contact with the torso 404 of the patient. In this manner the same device can be used with very little alteration to perform either left- or right-sided EKGs, allowing medical centers to stock just one device that can meet all their EKG electrode needs.

As illustrated in FIG. 4, the platform 402 is aligned on the torso 404 by positioning electrodes $V_R1$ and $V_R2$ in the fourth intercostal space and $V_R4$, $V_R5$, and $V_R6$ in the fifth intercostal space. Just as with the left-sided embodiment of FIG. 2a, the index marker 408 may then be configured to size after the initial alignment by tearing off the unneeded portion 413 of the marker 408 at the tear strips 414, in order to align the index marker 408 with an anatomical reference point such as the jugular notch 410, the angle of Louis 412 or the xiphoid process.

Next, electrode $V_R1$ on connector 420 is positioned to the left of the sternum, optionally guided by the reference marks 432, and locked into place. Electrode $V_R2$ on connector 422 is similarly positioned to the right of the sternum, optionally guided by reference marks 434, and locked into place. The same procedure is followed for the connectors on which are mounted electrodes $V_R3$ 424, $V_R4$ 426, $V_R5$ 428, and $V_R6$ 430, placing each in the mirror image position to where it was located for left-sided operation of the device. The signals received by the individual electrodes are again transmitted to the EKG machine via specific ones of the embedded wires via the end cap 440 and wire leads 442, or via the telemetry devices of FIG. 3.

Figure 5:
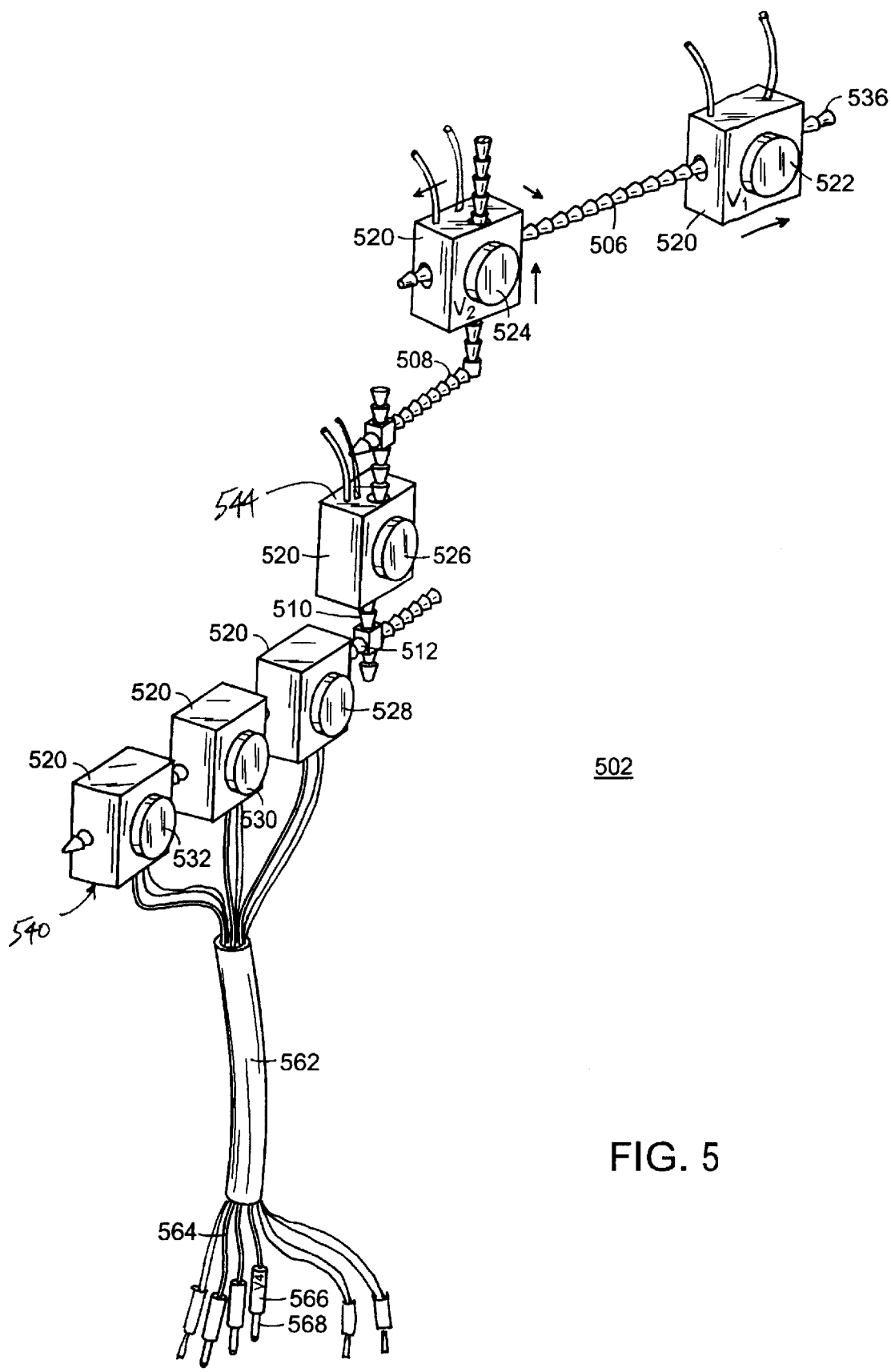
FIG. 5 is a reverse view of an alternate embodiment of the patient-specific precordial electrode system of the present invention, having articulating arms.

An alternate embodiment of the present invention is illustrated in FIG. 5. A totally integrated precordial electrode platform 502 has multiple articulating or telescoping arms, particularly adapted for folding, retracting, or collapsing the device for transport and storage. In the preferred embodiment of FIG. 5, the apparatus assumes a "reverse S" shape that allows optimum positioning of the electrodes. As shown in FIG. 5, electrodes V1 522 and V2 524 are mounted on upper arm 506, which is movably connected via middle arm 508 to vertical arm 510 on which is mounted electrode V3 526. Vertical arm 510 is then movably connected at its far end to lower horizontal arm 512 on which are mounted electrodes V4 528, V5 530, and V6 532.

For the telescoping embodiment, these movable connections allow the arms to be collapsed or retracted down upon themselves rather than, or in addition to, the rotational or folding movement contemplated by the articulating arm embodiment. The length of the vertical arm 510 is slidably adjustable at either the intersection with middle arm 508 or the intersection with lower horizontal arm 512 in order to allow the distance between upper horizontal arm 506 and lower horizontal arm 512 to be varied so that the electrodes may be positioned in the correct intercostal spaces. The telescoping embodiment is adjustable in the same manner.

Each electrode is independently mounted on its respective arm via a slidable mounting pad 520 that fits around the articulating arm. The position of each electrode mounting pad 520 may be freely adjusted along its respective arm until it reaches the proper alignment, as discussed previously. The position of the electrode pad 520 then snaps in and becomes fixed into the proper position by the serrated teeth or other type of ridge-like protrusions 536 present along the surface of each arm. The electrode is mounted on the pad so that it is in direct contact with the patient and may of course be used with standard electrode conducting gel. As with the embodiment of FIG. 2a, the embodiment of FIG. 5 is preferably constructed of an easily washable material. The preferred embodiment of FIG. 5 also may incorporate a set of limb leads, such as the ones in described in conjunction with FIG. 3.

Initial alignment of the integrated precordial electrode platform 502 is performed as described for previous embodiments of the invention. After the initial alignment, the platform 502 may be quickly aligned for subsequent tests by using an index marker such as is described and illustrated in FIG. 2a. In the alternative, optional permanently adjustable shoulder anchors may be provided for easy and consistent vertical and horizontal alignment on the patient. These shoulder anchors may also optionally be provided with a cross-brace that locks in to assist in side-to-side alignment of the platform 502 on the patient. Shoulder anchors have the additional advantage that the device may be held relatively secure while the patient is upright and even active, such as during stress testing. Alternatively, an optional harness may be provided to accommodate upright activities by the patient. Once the platform 502 is properly aligned and the mounting pads 520 have all been fixed into position, the position of the platform 502 may also be stabilized by any of the other well-known methods in the art, such as the preferred water-resistant adhesive, suction cups, belts or straps.

Transfer of the signals from the electrodes of FIG. 5 to the EKG machine may be accomplished in any of the manners well-known in the art, preferably either by wire leads directly connected to the EKG machine or through embedded wireless communications via telemetry devices such as those discussed in conjunction with FIG. 3, one telemetry device, adaptor, or connector being mounted on the top of each mounting pad 520. Similarly, transfer of signals from the source of electrical energy is accomplished by use of the wire leads. Wire leads may alternatively be connected on the underside 540 of the mounting pad 520, or through the pad 520 from the top 544. In addition, the several or all of the leads may again be drawn together into a cable sheath 562 from which emerge individual leads 564 that may be left bare for connection to the EKG machine and source of electrical energy by any of the various well-known methods such as alligator clips or, preferably, may end in labeled 566 connectors 568 suitable for direct insertion into the EKG machine and source of electrical energy.

Figure 6A:
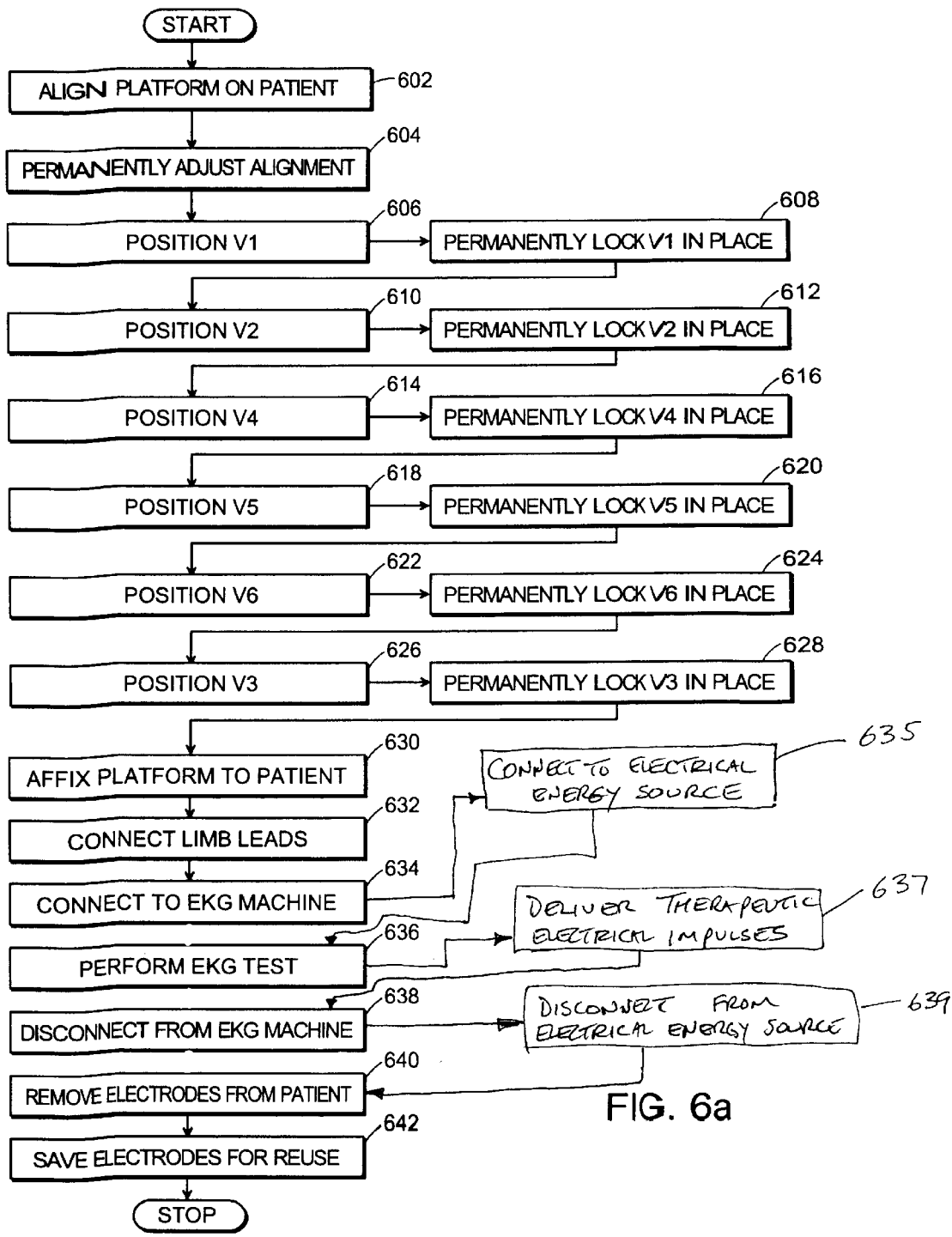

FIGS. 6a and 6b are block diagrams illustrating the method of cardiac mapping and measurement utilizing the EKG electrode positioning device of the present invention. As illustrated in FIG. 6a, initial positioning and adjustment of the EKG electrodes begins with proper alignment 602 of the precordial electrode platform on the patient so that electrodes V1 and V2 fall within the fourth intercostal space and V4, V5, and V6 fall within the fifth intercostal space. This may include adjustment of the length of the vertical section or arm of the platform. The alignment is then permanently adjusted 604 by marking or altering the index device extending between the precordial electrode platform and the chosen anatomical reference (e.g. the jugular notch or angle of Louis). At this point, the platform may optionally be configured for right-sided operation if desired, for example by removing and reversing the electrode mounts as described in conjunction with FIG. 4.

Electrode V1 is properly positioned 606 to the immediate right of the patient's sternum and then locked into place 608. Electrode V2 is similarly positioned 610 to the immediate left of the sternum and is also locked into place 612. Next, electrode V4 is positioned 614 on the midclavicular line and locked in 616, electrode V5 is positioned 618 on the anterior axillary line and locked in 620, and electrode V6 is positioned 622 at the midaxillary line and locked in 624. Finally, electrode V3 is positioned 626 halfway between V2 and V4 and locked in 628.

After the electrodes have all been properly positioned and locked into place, the now patient-specific precordial electrode platform may optionally be affixed 630 to the patient through the use of adhesives, suction cups, straps, or any other method known in the art. The four limb leads are next attached 632 to the patient, and then the leads from the six precordial electrodes and four limb leads are all connected to the EKG machine 634 in any convenient manner, often a manner that is dictated by the configuration of the EKG machine. The leads from the six precordial electrodes are also connected to the electrical energy source 635 in any convenient manner.

The EKG test is performed 636 in the normal manner, and therapeutic electrical impulses are delivered to the precordial electrodes 637. The electrical impulses may be transmitted to each precordial electrode simultaneously, or, alternatively, the impulses can be sequenced through the precordial electrodes in a predetermined manner. The electrical impulses can be transmitted to the heart essentially simultaneously with performance of the EKG test, thus saving time, which is critical in delivery of proper cardiac care. The electrode leads are then disconnected 638 from the machine and the electrical energy source 639 and the limb electrodes and precordial electrode platform may be removed from the patient 640. At this point, the patient-specific precordial electrode platform and limb leads may be retained by either the medical personnel or the patient for reuse for any subsequent EKG tests needed by that patient. A doctor or hospital may label the device with the specific patient's name and retain it in a centralized location, or the patient may be given the device to take with him or her for future use. Alternatively, the platform may of course be left in place on the patient for additional or subsequent testing.

Subsequent EKG testing utilizing the patient-specific EKG electrode positioning device of the invention is illustrated through the block diagram of FIG. 6b. After alignment 602 on the patient of the precordial electrode platform previously setup for the patient through the procedure of FIG. 6a, no further adjustment of the electrode position is necessary. Instead the technician proceeds straight to the optional step of affixing 630 the platform to the patient, followed by attachment of the limb leads 632, connection of the leads to the EKG machine 634 and to the electrical energy source 635, and performance 646 of the EKG test and delivery of therapeutic electrical impulses. After the procedures are completed, the leads are disconnected 638 from the machine and the source of electrical energy 639, the limb leads and precordial electrode platform may be removed 640 from the patient, and the precordial electrode platform and limb leads saved for reuse 642. Alternatively, the precordial electrode platform and/or limb leads may be left on the patient as the clinical situation dictates (e.g. if constant telemetry is needed). By using this method, a completely accurate and consistently reproducible EKG results and delivery of therapeutic electrical impulses to the heart are obtained quickly, efficiently, and with the bare minimum of setup time.

Figure 7:
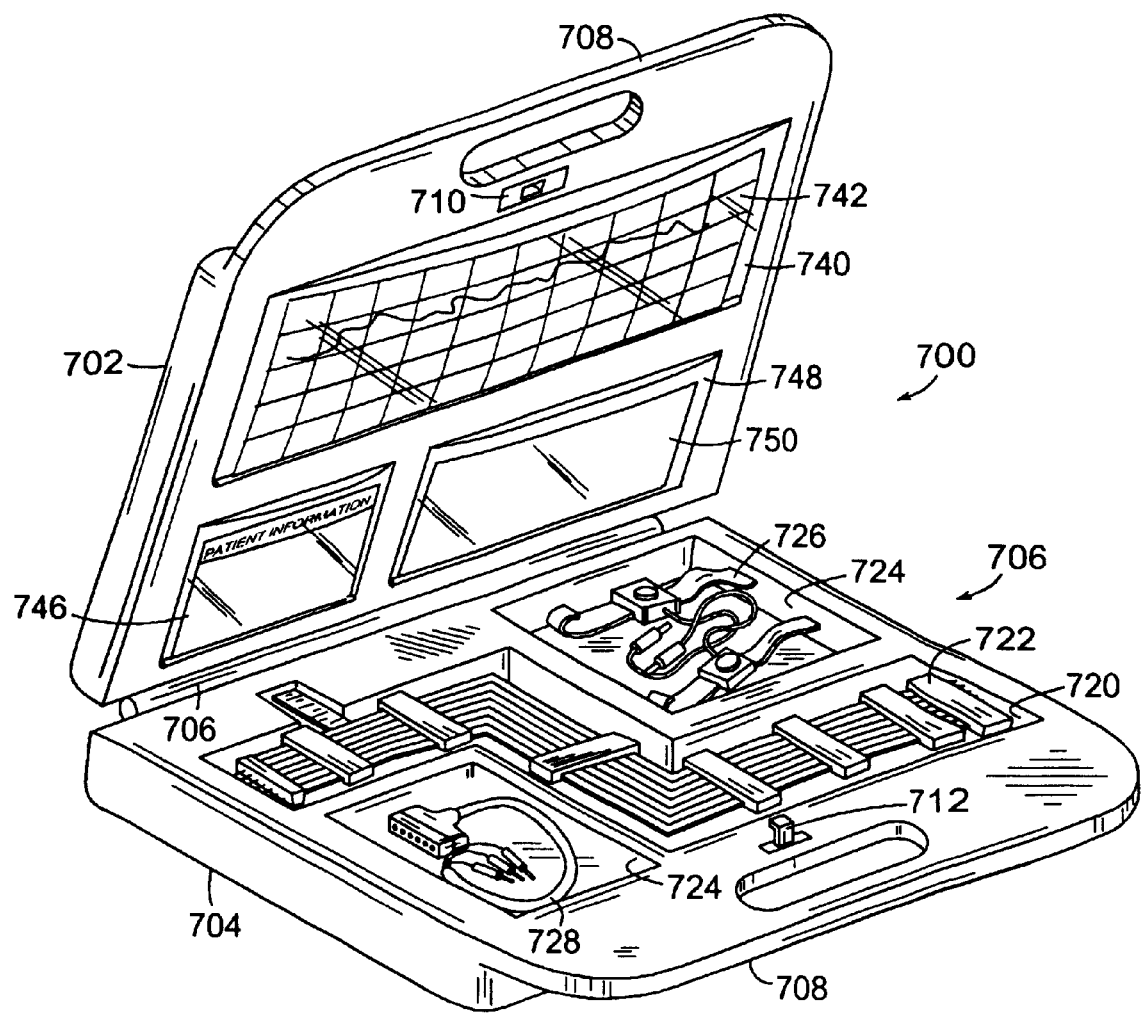
FIG. 7 illustrates a patient-specific EKG electrode kit including a carrying case, the precordial electrode of FIG. 2a, and several optional features.

One way in which a patient may retain the patient-specific device after initial setup is illustrated in FIG. 7. In this embodiment, the patient is provided with a carrying case 700 to hold the device, various optional accessories, and relevant informational materials. The device has a top cover or lid 702 and a bottom portion or base 704. In the preferred embodiment, the case 700 is made from molded plastic, but any type of rigid or semi-rigid material would be suitable. In the embodiment of FIG. 7, the lid 702 and base 704 are held to each other by two recessed hinges 706, but any convenient number or type of hinges or any other form of attachment known in the art would be suitable. As shown, the embodiment of FIG. 7 has a built-in handle 708 that is contiguously molded into the lid 702 and base 704, but any type of handle would be suitable and the handle could also be eliminated entirely if desired.

When in a closed configuration such that the lid 702 and base 704 are in complete contact, the carrier 700 is maintained in the closed position by a locking mechanism having top 710 and bottom 712 portions resident on the lid 702 and base 704 respectively. While a single push-button form of lock on the edges of the lid 702 and base 704 is illustrated, any form of locking mechanism known in the art, such as a buckle-type, twist-type, or even a keyed lock would be suitable, and whatever number of locking mechanisms found to be convenient may of course be employed.

Inside the base 704, the kit has a well 720 that is shaped and sized to hold the precordial electrode platform 722 of the invention without damage to the wires or electrode mounts. The embodiment of FIG. 2a is shown in FIG. 7, but the case 700 and well 720 could equally be shaped and used to hold the embodiment of FIG. 5, with or without folding of the articulating arms, or to hold any other embodiment of the invention. One or more additional wells 724 may further be provided to hold various optional accessories, such as a set of limb electrodes 726 or cabling device 728.

Inside the lid 702 are optional informational accessories and materials, including a preferably see-through plastic pouch 740 or other device for holding a base-line EKG tracing 742 for the patient taken using the precordial electrode platform 722. This base-line EKG tracing 742 is then always available to be used as the standard of comparison for all future tests performed on the patient using the platform 722. Other optional informational materials resident in the lid 702 may include a Patient Information card 746 to list information about the patient such as name, address, physician, blood type, allergies, cardiac history, medications, emergency notification numbers, etc. Additional optional pouches 748 may hold such materials as disease management pamphlets or records 750, or instructional materials for use of the electrode platform 722.

It is understood that the specific mechanisms and techniques described are merely illustrative of some of the applications of the principles of the invention. Modifications and substitutions by one of ordinary skill in the art to the methods and apparatus described are considered to be within the spirit and scope of the present invention, which is not to be limited except by the claims which follow.

What is claimed is:

1. A patient-specific apparatus for consistent electrode positioning for EKG testing and delivery of therapeutic electrical impulses to a heart, comprising, in combination:
    a precordial electrode platform;
    a plurality of precordial electrodes, each precordial electrode being attached to said precordial electrode platform in a manner initially non-fixed with respect to said precordial electrode platform and each other;
    means for permanently retaining the position of each of said precordial electrodes on said precordial electrode platform after proper positioning of each of said precordial electrodes on a particular patient for EKG testing and defibrillation;
    means for transmitting the signals received via said precordial electrodes to an EKG machine;
    means for transmitting electrical energy to said precordial electrodes; and
    an adjustable position indicator for initial proper positioning of said precordial electrode platform on said particular patient.

2. The apparatus of claim 1, wherein said plurality of precordial electrodes comprises the six standard precordial electrodes commonly used for an EKG test.

3. The apparatus of claim 1, further including means for initially guiding proper positioning of each of said precordial electrodes on said particular patient.

4. The apparatus of claim 3, wherein said means for initially guiding proper positioning of said electrodes comprises marked areas on said precordial electrode platform.

5. The apparatus of claim 1, wherein said means for initial proper positioning of said platform is an adjustable measurement strip attached to said precordial electrode platform.

6. The apparatus of claim 5, wherein said measurement strip is initially aligned to the jugular notch of said particular patient, said measurement strip being permanently adjustable at first placement of said precordial electrode platform on said particular patient so that subsequent alignment of said measurement strip to said jugular notch will instantly properly position said precordial electrode platform on said particular patient.

7. The apparatus of claim 5, wherein said measurement strip is initially aligned to the angle of Louis of said particular patient, said measurement strip being permanently adjustable at first placement of said precordial electrode platform on said particular patient so that subsequent alignment of said measurement strip to said angle of Louis will instantly properly position said precordial electrode platform on said particular patient.

8. The apparatus of claim 5, wherein said measurement strip is initially aligned to the xiphoid process of said particular patient, said measurement strip being permanently adjustable at first placement of said precordial electrode platform on said particular patient so that subsequent alignment of said measurement strip to said xiphoid process will instantly properly position said precordial electrode platform on said particular patient.

9. The apparatus of claim 1, wherein said means for transmitting electrical energy comprises wire leads.

10. The apparatus of claim 1, wherein electrical energy transmitted to said precordial electrodes provides defibrillation.

11. The apparatus of claim 1, wherein electrical energy transmitted to said precordial electrodes provides external pacemaker therapy.

12. The apparatus of claim 1, wherein electrical energy transmitted to said precordial electrodes provides cardioversion of tachydysrhythmias.

13. A patient-specific electrode platform for EKG testing and delivery of therapeutic electrical impulses to a heart, comprising, in combination:
    a flexible electrode platform, said flexible electrode platform further having two sets of embedded wires, a first set of the embedded wires being individually connectable to an EKG machine and a second set of the embedded wires being individually connectable to a source of electrical energy;
    a set of precordial EKG electrodes, each precordial electrode slidably attached along said flexible electrode platform in an initially non-fixed manner;
    means for permanently connecting each one of said precordial electrodes to a pre-specified one of said embedded wires in each of the two sets of embedded wires, such that each of said precordial electrodes will be attached to both one of said embedded wires that is connectable to an EKG machine input configured to receive signals from said electrode and to one of said embedded wires that is connectable to an output of the electrical energy source configured to send a signal to said electrode;
    means for permanently fixing and maintaining the position of each of said precordial electrodes on said flexible electrode platform after proper initial positioning of each of said precordial electrodes on a particular patient for EKG testing and delivery of therapeutic electrical impulses;
    an adjustable position indicator for proper positioning of said flexible electrode platform on said particular patient;
    means for guiding proper initial positioning of each of said precordial electrodes on said particular patient; and
    means for maintaining contact between said flexible electrode platform and said particular patient after proper positioning of said flexible electrode platform on said patient in order to ensure proper contact between said precordial electrodes and said patient.

14. The apparatus of claim 13, wherein said adjustable position indicator works by alignment to a pre-specified and easily recognizable site on the body of said patient.

15. A method for consistent positioning of a set of electrodes for EKG testing and delivery of therapeutic electrical impulses to a heart, comprising, in combination, the steps of:

- movably pre-attaching a plurality of precordial electrodes to a precordial electrode platform;
- properly positioning said precordial electrode platform on a particular patient with an adjustable position indicator provided on said platform;
- properly positioning each of said precordial electrodes on said patient by sliding each of said precordial electrodes along said precordial electrode platform;
- permanently fixing and maintaining the position of each of said properly positioned precordial electrodes on said precordial electrode platform;
- maintaining proper constant contact between said precordial electrode platform and said patient at all times after proper positioning of said platform on said patient;
- transmitting the signals received from said precordial electrodes to an EKG machine; and
- transmitting therapeutic electrical impulses from a source of electrical energy to said precordial electrodes.

16. The method of claim 15, wherein the step of transmitting therapeutic electrical impulses from a source of electrical energy to said precordial electrodes includes simultaneous transmission of impulses of energy to each electrode.

17. The method of claim 15, wherein the step of transmitting therapeutic electrical impulses from a source of electrical energy to said precordial electrodes includes transmitting impulses of energy to each electrode in a predetermined sequence.

18. The method of claim 15, further including the step of reusing said precordial electrode platform on said particular patient after said precordial electrode platform has first been removed from and then replaced on said patient.

19. The method of claim 15, further including the steps, in combination, of:

- reversing the orientation of said precordial electrodes on said precordial electrode platform before said precordial electrodes have been permanently fixed to said platform; and
- reversing the orientation of said platform on said patient in order to obtain an opposite-sided EKG tracing.

20. A patient-specific apparatus for consistent positioning of electrodes for EKG testing and delivery of therapeutic electrical impulses to a heart, comprising, in combination:

- a precordial electrode platform;
- a plurality of precordial electrodes, each precordial electrode being attached to said precordial electrode platform in a manner initially non-fixed with respect to said precordial electrode platform and each other;
- a plurality of clamping members, each clamping member for permanently retaining the position of one of said precordial electrodes on said precordial electrode platform after proper positioning of each of said precordial electrodes on a particular patient for EKG testing and delivery of therapeutic electrical impulses;
- a plurality of wire leads for transmitting the signals received via said precordial electrodes to an EKG machine;
- a plurality of wire leads for transmitting signals from a source of electrical energy to said precordial electrodes; and
- an adjustable position indicator for initial proper positioning of said precordial electrode platform on said particular patient.

* * * * *

UNITED STATES PATENT AND TRADEMARK OFFICE
CERTIFICATE OF CORRECTION

PATENT NO. : 6,400,975 B1
DATED : June 4, 2002
INVENTOR(S) : McFee

It is certified that error appears in the above-identified patent and that said Letters Patent is hereby corrected as shown below:

<u>Title page,</u>
Item [*] Notice, delete the phrase "by 0 days" and insert -- by 77 days --

Signed and Sealed this

Twenty-first Day of September, 2004

JON W. DUDAS
*Director of the United States Patent and Trademark Office*